US011273273B2

(12) United States Patent
Maguire

(10) Patent No.: US 11,273,273 B2
(45) Date of Patent: Mar. 15, 2022

(54) APPARATUS AND METHOD FOR CONVERTIBLE VOLUME AND PRESSURE-CONTROLLED LUNG-PROTECTIVE VENTILATION

(71) Applicant: AirMid Critical Care Products, Inc., Washington, DC (US)

(72) Inventor: Michael D. Maguire, Washington, DC (US)

(73) Assignee: AirMid Critical Care Products, Inc., Washington, DC (US)

( * ) Notice: Subject to any disclaimer, the term of this patent is extended or adjusted under 35 U.S.C. 154(b) by 0 days.

(21) Appl. No.: 17/216,221

(22) Filed: Mar. 29, 2021

(65) Prior Publication Data

US 2021/0299372 A1    Sep. 30, 2021

Related U.S. Application Data

(60) Provisional application No. 63/001,911, filed on Mar. 30, 2020.

(51) Int. Cl.
*A61M 16/00* (2006.01)
*A61M 16/20* (2006.01)
*A61M 16/06* (2006.01)

(52) U.S. Cl.
CPC ........ *A61M 16/0084* (2014.02); *A61M 16/06* (2013.01); *A61M 16/209* (2014.02);
(Continued)

(58) Field of Classification Search
CPC .......... A61M 16/0081; A61M 16/0057; A61M 16/0078; A61M 16/75; A61M 16/08; A61M 16/0075; A61M 16/0084
See application file for complete search history.

(56) References Cited

U.S. PATENT DOCUMENTS

| 5,520,173 A | * | 5/1996 | Kuhn | A61M 16/0084 |
| | | | | 128/205.13 |
| 6,155,257 A | | 12/2000 | Lurie et al. | |

(Continued)

FOREIGN PATENT DOCUMENTS

| DE | 2945472 A1 | * | 5/1981 | ............ A61M 16/00 |
| GB | 2052270 A | * | 1/1981 | .......... A61M 16/009 |
| WO | 2017118962 A1 | | 7/2017 | |

OTHER PUBLICATIONS

Mark A Warner, "Chapter 48: Mechanical Ventilation", Benumof and Hagberg's Airway Management 2013, Elsevier, Third Edition, p. 981 (Year: 2013).*

*Primary Examiner* — Kathryn E Ditmer
(74) *Attorney, Agent, or Firm* — Proskauer Rose LLP

(57) ABSTRACT

A system for actuating a volume and/or pressure-controlled manual ventilator including a manual ventilator, a storage case, and an actuating mechanism. The manual ventilator includes a compressible body, an output one-way valve at an output end, and an input one-way valve at an input end. The storage case includes an inner housing surface configured to accommodate the manual ventilator. The actuating mechanism includes a power unit mechanically coupled to a linear rod mechanism and one or more applicator pads mechanically coupled to the linear rod mechanism and proximal to the compressible body. The linear rod mechanism is configured to convert a rotating motion of the power unit into an axial movement of the linear rod mechanism. The actuating mechanism is configured to apply pressure to the compressible body of the manual ventilator via the one or more applicator pads such that a volume of the compressible body is deflated.

19 Claims, 12 Drawing Sheets

(52) U.S. Cl.
CPC . *A61M 2205/50* (2013.01); *A61M 2205/8206* (2013.01); *A61M 2240/00* (2013.01); *A61M 2250/00* (2013.01)

(56) References Cited

U.S. PATENT DOCUMENTS

| | | | | |
|---|---|---|---|---|
| 8,534,282 | B2* | 9/2013 | Bergman | A61M 16/0084 128/205.16 |
| 2005/0284472 | A1* | 12/2005 | Lin | A61M 16/0084 128/202.29 |
| 2006/0191536 | A1* | 8/2006 | Kroupa | A61M 16/209 128/205.13 |
| 2011/0041852 | A1 | 2/2011 | Bergman | |
| 2019/0232016 | A1 | 8/2019 | Sayani et al. | |
| 2019/0336713 | A1 | 11/2019 | Piracha et al. | |
| 2020/0086075 | A1* | 3/2020 | Mujeeb-U-Rahaman | A61M 16/0078 |

* cited by examiner

APPARATUS AND METHOD FOR CONVERTIBLE VOLUME AND PRESSURE-CONTROLLED LUNG-PROTECTIVE VENTILATION

CROSS REFERENCE TO RELATED APPLICATION

This application claims the benefit of and priority to U.S. Provisional Patent Application No. 63/001,911, filed Mar. 30, 2020, the entire contents of which are owned by the assignee of the instant application and incorporated herein by reference in their entirety.

FIELD OF THE INVENTION

The present invention relates generally to the field of medical equipment for critical care and life support, and more specifically to the process of delivering either automated or manual (i.e., hand-operated) artificial ventilation during the course of medical or veterinarian care.

BACKGROUND OF THE INVENTION

There are a number of medical conditions whereby a patient, being either human under the care of medical providers or an animal under veterinary care (collectively referred to here as patients), are unable to maintain their own life-sustaining breathing function without a degree of mechanical assistance. For example, patients whose breathing reflexes have been suppressed through pharmacologic, traumatic or physiologic paralysis may have completely absent respiratory effort, leading to a condition that will rapidly lead to death if breathing function is not provided via an external means. Other patients may have underlying trauma or pathophysiologic conditions causing markedly elevated work of breathing, such that progressive fatigue will result in diminishing respiratory function to a point where breathing stops. Such conditions where normal breathing function is replaced by external means is known in the art as artificial ventilation (and more colloquially as artificial "respiration" or being on "life support").

Artificial ventilation can generally be achieved through means of applying either positive or negative pressure to the patient in such a way to cause the lungs to inflate and deflate. Positive pressure artificial ventilation is achieved by creating a positive pressure gradient in the lungs relative to ambient atmospheric pressure, thereby causing the lungs to inflate. Alternatively, negative pressure artificial ventilation is achieved with an approach whereby a patient's chest is surrounded by an air-tight container with the head protruding, and with subsequent ability for a vacuum to be applied to that portion of the body residing in the chamber in such a way as it causes active expansion of the chest and lung inflation through a negative pressure gradient in the lungs relative to atmospheric pressure. Negative pressure artificial ventilation closely reproduces natural respiratory function, the latter of which is achieved through thoracic muscle and diaphragm movement that expands the chest wall creating a vacuum inside the lungs that subsequently draws air into the lungs under a gentle negative pressure. However the need to surround the thorax by a large chamber presents several problematic issues (such as size and inability to access the patient for care), leading to positive pressure ventilation generally comprising the method employed to provide artificial ventilation to patients.

SUMMARY OF THE INVENTION

In accordance with the present invention, a method and apparatus is provided for "convertible ventilation" whereby a singular apparatus can be used to deliver both manual and/or mechanical ventilation.

It is an object of the current invention to be able to provide volume and/or pressure-controlled manual ventilation in compliance with lung-protective guidelines in either manual or mechanical mode, thereby addressing current inability of users to safely protect patients from accidental, inadvertent over-inflation when manually initiating artificial ventilation and/or providing manual ventilation during periods when mechanical ventilation is not possible.

It is a further object of the current invention that it provides a means to convert from manual volume and/or pressure-controlled ventilation to mechanical volume and/or pressure-controlled ventilation utilizing a simplified mechanism that does not need to provide for volume and/or pressure-control, as those safety elements are incorporated into the manual ventilator portion of the invention, thereby enabling more intuitive and rapid transition of patient care from manual to mechanical modes.

The current invention also provides a novel approach to deliver volume and/or pressure-controlled mechanical ventilation resulting in a simpler mechanism compared to existing mechanical ventilators in the field, thereby enabling mechanical ventilation to be more financially accessible to those care venues relative to current mechanical ventilators in the field that are prohibitively expensive.

It is a further object of the present invention that it can be used without a compressed gas source if necessary, further simplifying its operation in both manual and mechanical modes.

An additional object of the present invention is that, due to the aforementioned objects and advantages providing a simplified and more intuitive apparatus compared to conventional mechanical ventilators, that the present invention can be safely used by non-specialists in the field, thereby providing a means for lung-protective manual and/or mechanical ventilation to be universally accessible to patients without regard to whether they are being cared for by layperson bystanders, out-of-hospital first responders, lifeguards, emergency medical technicians and paramedics, or in-hospital by any care provider of various skill level in the art.

Another object of the invention is that it is readily convertible between manual and mechanical modes, whereby the volume and/or pressure-controlled manual ventilator is easily accessible when contained in the storage case such that, to initiate volume and/or pressure-controlled manual ventilation, the user need only withdraw the volume and/or pressure-controlled manual ventilator from the storage case and begin employing it without delay. Further, to rapidly and intuitively convert from manual to mechanical ventilation, the operator need only place the volume and/or pressure-controlled manual ventilator into the storage case, whereby the storage case mechanical actuating action will commence to transition the patient to automated volume and/or pressure-controlled mechanical ventilation.

Finally, to address various venues of care and global disparities in resources, it is an object of the invention that the actuating action can be powered by electrical, pneumatic, or mechanical energy storage means, including specific embodiments that may be capable of operating under one or more approaches to powered operation.

Accordingly, one aspect of the present invention includes (1) a volume and/or pressure-controlled manual ventilator and (2) a storage case for the volume and/or pressure-controlled manual ventilator, the latter containing an actuating mechanism capable of effecting action on the volume and/or pressure-controlled manual ventilator such that the actuating action results in function of the volume and/or pressure-controlled manual ventilator contained within. Notably, the present invention achieves mechanical volume and/or pressure-controlled ventilation through a novel and unintuitive means, whereby the volume and/or pressure control means is not inherent to the actuating apparatus, but is instead provided by the volume and/or pressure-controlled manual ventilator component of the present invention, thereby obviating complexity that would otherwise be required in the storage case actuating mechanism in order to achieve volume and/or pressure-controlled mechanical ventilation when the convertible ventilator is being used in mechanical mode.

Another aspect of the present invention facilitates conversion between manual and mechanical artificial ventilation modes. To initiate volume or pressure-controlled manual ventilation, the volume and/or pressure settings located on the volume and/or pressure-controlled manual ventilator can be selected while the volume and/or pressure-controlled manual ventilator remains in the storage case and/or adjusted after removal from the storage case. The volume and/or pressure-controlled manual ventilator may be stored in readiness with attachments specific to manual mode (e.g., one-way valve, face mask, oxygen reservoir) already connected in order to minimize time and steps needed to initiate volume and/or pressure-controlled manual ventilation. To transition to mechanical mode, attachments specific to the volume and/or pressure-controlled manual ventilator can be quickly removed, the volume and/or pressure-controlled manual ventilator placed back into the storage case, and attachments specific to mechanical mode quickly connected. Once in mechanical mode, various adjustments can be made to ventilation delivery settings. Additionally, alarm mechanisms contained within the storage case can be programmed in order for the patient to remain under automatic mechanical ventilatory support without direct supervision by qualified personnel.

The embodiments of the present invention are inherently compact in size in both manual and mechanical modes, making them suitable for use in out-of-hospital venues of care and/or during patient transport. The outer housing of the storage case is preferentially fitted with clamps and/or receptacles such that it can be easily fastened to a hospital bed, stretcher, gurney, combat litter, or other modality associated with patient care.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

Figure 1:
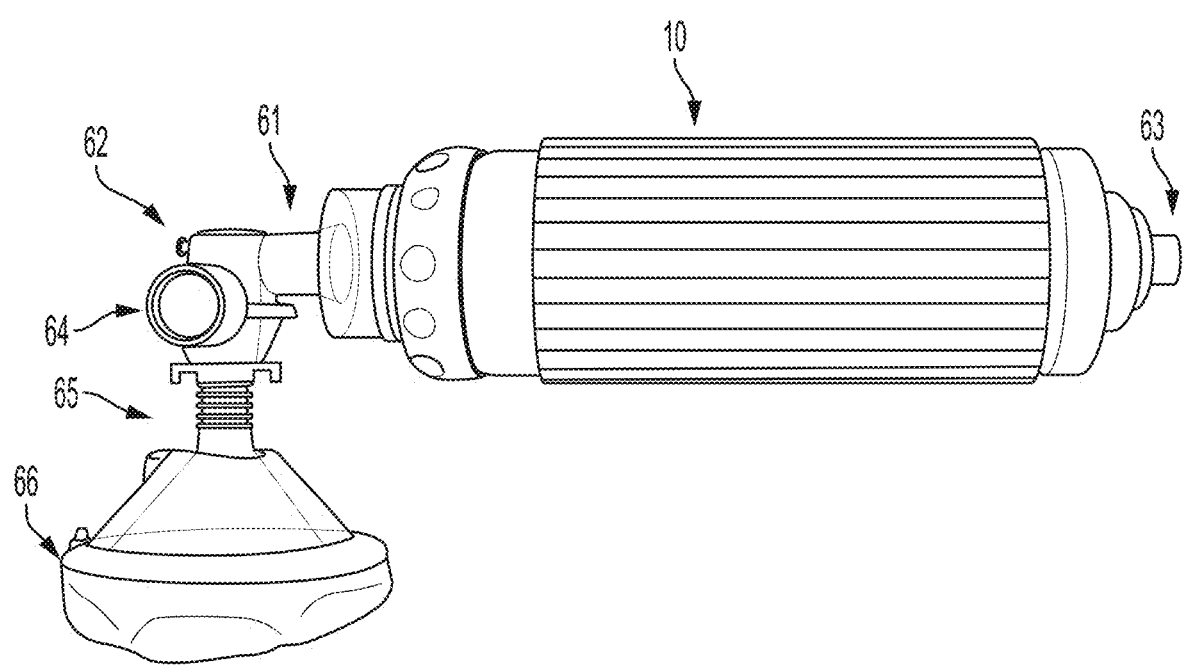
FIG. 1 is a perspective view of a volume and/or pressure-controlled manual ventilator, according to an embodiment of the invention.

Among various positive pressure artificial ventilation adjuncts common to the art, all are generally categorized as either mechanical or manual. Mechanical ventilators are medical devices capable of providing autonomous artificial ventilation to patients. These are generally powered by electrical means, while other mechanical ventilators—particularly those intended for out-of-hospital use—can be powered by a compressed gas source that enables the device to operate via pneumatic propulsion. In contrast, manual artificial ventilators are human-powered, meaning they only function when physically operated by a human operator under a manual effort that generates the positive pressure needed to deliver a breath to a patient.

Several modalities of artificial manual ventilator are present in the art, ranging from a simple pocket face mask enabling the operator to manually deliver breaths using their own exhaled breaths, up to a more elaborate but still simple device connected to a patient that enables air to be displaced into patients when a breathing gas reservoir is manually squeezed by the operator. Similarly, there are significant variations in mechanical ventilators, however all are necessarily more complex than manual ventilators due to the need to provide for output adjustments such that the mechanical ventilator can be adjusted to provide tailored or precision breaths in accordance with each individual patients' anatomy and physiologic requirements. Such adjustments include the concentration of oxygen, breath size (typically expressed in milliliters), inspiratory time (the time over which each breath is delivered), and ventilation rate (the total number of breaths delivered per minute). More sophisticated ventilators include airway pressure limits, the ability for "inspiratory pause" when the lung is fully inflated (which is highly diagnostic as a tool to measure inherent stretch resistance—called compliance—of the lungs), as well as other sensor-based features enabling mechanical ventilators to work in concert with a patient's own breathing efforts, particularly as a measure to help a patient regain strength to eventually resume their own unassisted breathing function (known in the art as "weaning").

With regards to setting breath size (or tidal volume) in accordance with artificial mechanical ventilation, there are two primary approaches generally seen in the field. In volume-controlled artificial mechanical ventilation, a specific breath size is specified in terms of volume (typically expressed in milliliters), whereby the apparatus delivers that set volume independent of the airway pressure required to overcome both airway resistance and lung compliance. In contrast, in pressure-controlled artificial ventilation, a specific maximum airway pressure is set (typically expressed in centimeters of water pressure), whereby lung inflation will continue toward an unspecified breath volume until such a time as the maximum pressure setting equals the inherent resistance of the lungs and thoracic cavity. Pressure-controlled ventilation is most often employed on neonatal and pediatric patients (and small animals), while volume-controlled ventilation is typically employed on larger patients.

In contrast to mechanical ventilators, manual ventilators typically lack any ability to provide specific artificial ventilation parameters—instead, operators subjectively attempt to exercise good judgement when manually delivering breaths to deliver appropriate breath size, rate, inspiratory time, and other variables that are typically specifically set on mechanical ventilators. Manual ventilators currently used in the field are therefore "uncontrolled" devices.

While several embodiments for manual ventilators exist, bag-type ventilators are the most prominent. These devices comprise a hand-squeezable bag with two or more one-way valves that result in flow being directed to the patient when the bag is squeezed, with patients' expired air being directed to the atmosphere during exhalation. Manual bag ventilators are also substantially of two types. Flow-inflating bag ventilators comprise a bag material that has no inherent inflation/deflation mode, whereby a constant external pressurized gas source is required to inflate the bag prior to the bag being able to be manually hand-squeezed to deliver a breath. Flow-inflation bags are almost exclusively used in anesthesia applications where a constant pressurized gas source is always present, and where the composition of breathing gas needs to be highly specific and contain required concentrations of anesthetic components. Consequently, flow-inflation bags are predominantly seen attached to anesthesia delivery unit machines. Additionally, due to the extreme delicate nature of pre-term infants, specialized stand-alone flow-inflation bags are also occasionally seen in delivery suites, as well as other in-hospital critical care venues when preferred by highly specialized users. Notably, flow-inflating bags cannot function without a compressed gas source, making them largely unsuitable during emergencies, during patient transport, and in out-of-hospital settings. In contrast, self-inflating manual ventilation bags—the second type—are almost exclusively found in all out-of-hospital venues, while, in-hospital, self-inflating bags predominate outside neonatal and anesthesia venues of care. Unlike flow-inflating bags, the material used in self-inflating bags have elastic and/or memory capability such that, after a hand-squeezed breath is delivered by compression applied to the bag, removal of the compression force result in the properties of the bag material causing it to recoil, thereby providing self-inflation functionality enabling the bag to resume its normal inflated position in preparation for delivery of the next breath. Self-inflating manual bag ventilators can therefore be used without any requirement for an external gas source, however a connection for supplemental oxygen is generally provided so higher concentrations of oxygen can be used to deliver breaths if required.

Several important distinctions are apparent in the field in relation to manual vs mechanical ventilators. Manual ventilators are simple devices that are inexpensive, typically disposable after single-patient use, small and light in size, and require no electrical or pneumatic power in order to operate. For these reasons, manual ventilators almost invariably constitute the first tier of artificial ventilation as, due to their low cost, they can be inexpensively placed in multiple places throughout hospitals and in out-of-hospital responder kits so as to be readily accessible without delay for emergencies. As a result, manual ventilators are generally stored in readiness in plain view in all emergency treatment rooms, on all emergency "crash" carts, in all intensive care units (ICUs), and—as a backup—wherever a mechanical ventilator is in use. Outside hospitals, manual ventilators are found in virtually every first response vehicle, ambulance, and outpatient clinic (particularly those where sedation is used). Similar staging and use of manual ventilators is common in military, disaster response, and other contingency applications. Due to the inherent simplicity of manual bag-type ventilators, broad tiers of personnel are easily trained in their use, ranging from entry-level medical technicians to include lifeguards, emergency medical technicians, paramedics, nurses and physicians. Finally, due to the inherent nature of manual ventilators to require human operation, their use is typically temporary until such time as a patient requiring sustained ventilation can be placed on a mechanical ventilator. However, in some settings manual ventilation may last up to an hour or, in developing countries, potentially for days. For example, most ambulance services cannot afford mechanical ventilators, particularly those services that serve rural areas. The need for artificial ventilation in these settings usually lasts the length of on-scene care and transport to a hospital. Additionally, global socio-economic disparities result in manual ventilators being used for much longer periods of time due to insufficient financial resources and infrastructure required for current mechanical ventilators.

In contrast to manual ventilators, mechanical ventilators require electrical power and/or a source of compressed gas in order to operate, limiting their portability. Further, when patients require artificial ventilation for days or weeks, then additional sophistication and settings as previously mentioned are often required in order to provide highly tailored breath delivery in accordance with individual patients' specific anatomic lung characteristics and underlying pathology. Advanced sophistication necessarily adds complexity, resulting in a physically larger unit—some being self-standing, bedside units—as well as preparatory steps that need to be taken before the unit is ready to be connected to a patient. Increased size and complexity also adds significant cost, such that mechanical ventilators are generally too expensive to store in every hospital room just in the event a patient may need one emergently.

In addition to complexity and cost surrounding mechanical ventilators themselves, there is also secondary expense associated with the need for specialized personnel specifically trained in their use. Typically, only ICU physicians (e.g., intensivists and pulmonologists) are fully trained in prescribing long-term ventilator settings, while respiratory therapists comprise an entirely separate career field in the medical arts that, in part, provide for the necessary specialized aptitude required for mechanical ventilator setup, settings, and maintenance.

All of these factors limit suitability of mechanical ventilators as first-line devices to institute artificial ventilation, as it is not feasible for non-breathing patients to remain without artificial ventilatory support while it takes time for a mechanical ventilator to be brought to the patient and set up by specialized personnel. These reasons contribute to barriers preventing widespread adoption of mechanical ventilators for use outside hospitals.

Accordingly, delivery of artificial ventilation almost invariably follows two phases of care. Artificial ventilation is initiated with a manual ventilator, even during routine anesthesia induction during the course of surgery. In emergencies, a manual ventilator is the first artificial ventilator that becomes available for use regardless of in-hospital or out-of-hospital venue of care. In out-of-hospital settings, or in-hospital settings where a mechanical ventilator is unavailable, manual ventilation continues beyond initiation for that period of time required for it to be no longer needed (due to patient recovery or death) or until the patient is able to be transitioned to a mechanical ventilator (which, outside surgery, means a mechanical ventilator is typically not immediately at hand).

Once a patient is able to be transitioned from manual to mechanical ventilation, there are still times when it is necessary to transition back to manual ventilation. As previously described, mechanical ventilators often lack portability, so a requirement to transport a patient within a hospital often necessitates a period of manual ventilation during movement. For example, patients mechanically ventilated during surgery that need to remain artificially ventilated during subsequent ICU recovery are often removed from sophisticated mechanical ventilation provided by the anesthesia delivery unit, manually ventilated during movement to the ICU, and then placed back on an ICU mechanical ventilator with highly specific settings for each particular patient. Patients under mechanical ventilation in an ICU must also occasionally be transitioned back to manual ventilation during transport to other areas of a hospital for computed tomography (CT) and/or magnetic resonance imaging (MRI) diagnostic testing, and/or to specialized treatment rooms where certain interventional procedures not suitable for the ICU setting are conducted. Finally, manual ventilation is also typically immediately employed as a back-up when a mechanical ventilator requires maintenance, is thought to be malfunctioning, or fails (such as during a power loss, or when a pneumatically-driven mechanical ventilator stops functioning when the compressed gas source becomes depleted). As a result, patients undergoing long-term mechanical ventilation are invariably also exposed to periods of manual ventilation that last minutes to up to an hour (or even longer when a mechanical ventilator is not immediately available, as previously described).

In accordance with the inherent difference in sophistication between manual and mechanical ventilation, there is significant disparity in patient safety between the two modes. Mechanical ventilators are capable of precise and tailored breath delivery, while manual ventilators lack built-in breath management settings and are thus effectively uncontrolled devices. There is robust peer-reviewed research demonstrating that, regardless of training, providers attempting to exercise good subjective judgment using manual bag-type ventilators routinely fail at this task. A study of providers' ability to deliver breath sizes within patients' natural lung capacities demonstrated that even physicians accidently over-inflated beyond natural lung capacity over 72% of the time. [Bassani M A, Filho F M, de Carvalho Coppo M R, Marba S T M. An evaluation of peak inspiratory pressure, tidal volume, and ventilatory frequency during ventilation with a neonatal self-inflating bag resuscitator. *Respiratory Care* 2012; 57:525-530.] An observational human clinical investigation assessed physicians' use of manual bag ventilators on human cardiac arrest patients, demonstrating highly variable breath sizes were delivered with some possibly exceeding natural lung capacity by two-fold or more. [O'Neill J F, Deakin C D. Do we hyperventilate cardiac arrest patients? *Resuscitation* 2007; 73, 82-85.] Inability to control lung inflation is now known to be a direct cause of Acute Lung Injury (ALI), now more specifically referred to as Ventilation-Induced Lung Injury (VILI), with over-inflation causing direct tearing of delicate lung tissue from over-stretch. The injury pattern of VILI results in lung inflammation that results in less ability to oxygenate the blood. If over-stretch is minor, lung injury may simply result in a need for supplemental oxygenation and hospitalization until the lungs are able to heal. However moderate lung injury often results in separate and/or prolonged mechanical ventilation with high concentrations of oxygenation necessary to sustain life.

Additional peer-reviewed research demonstrates that, if patients are protected from over-inflation, then severity of VILI/ALI can be mitigated or even completely averted in its entirety. The findings of a research collaboration in 2000 confirmed that not over-inflating the lungs of ICU patients that already had ALI facilitated healing that improved mortality by approximately 28%. This study effectively established what is now a definitive guideline for delivering lung-protective ventilation [Acute Respiratory Distress Syndrome Network: Brower R G, Matthay M A, Morris A, Schoenfeld D, Thompson B T, Wheeler A. Ventilation with lower tidal volumes as compared with traditional tidal volumes for acute lung injury and the acute respiratory distress syndrome. *N Engl J Med.* 2000 May 4; 342(18): 1301-1308.] More recent studies showed that adhering to the lung-protective guideline in patients without lung injury actually prevents VILI from occurring at all by a rate of approximately 61.8% and 62.0% (respectively). [Futier E, Constantin J M, Paugam-Burtz C, Pascal J, Eurin M, Neuschwander A, Marret E, Beaussier M, Gutton C, Lefrant J Y, Allaouchiche B, Verzilli D, Leone M, De Jong A, Bazin J E, Pereira B, Jaber S; IMPROVE Study Group. A trial of intraoperative low-tidal-volume ventilation in abdominal surgery. *N Engl J Med.* 2013 Aug. 1; 369(5):428-37; and Fuller B M, Ferguson I T, Mohr N M, Drewry A M, Palmer C, Wessman B T, Ablordeppey E, Keeperman J, Stephens R J, Briscoe C C, Kolomiets A A, Hotchkiss R S, Kollef M H. Lung-protective ventilation initiated in the emergency department (LOV-ED): A quasi-experimental, before-after trial. *Ann Emerg Med.* 2017 September; 70(3):406-418. also appearing in *BMJ.* 2016 Apr. 11; 6(4).] The latter study, which assessed the impact of employing lung-protective ventilation on patients in the emergency room and very shortly after initiating artificial ventilation, found that protecting patients from accidental over-inflation during an earlier phase of care resulted in a sharp decrease in severe hospital-caused VILI, resulting in an improved rate of patient survival of 42.5%.

This peer-reviewed evidence, demonstrating both that (1) failure to adhere to lung-protective guidelines, even for relatively short periods, can be fatal by directly causing VILI, and (2) that regardless of training, providers endemically over-inflate when using manual bag ventilators, making guideline-compliance unattainable, clearly demonstrates a need for a manual bag-type ventilator capable of adhering to the lung-protective guidelines. The need for such a device was anticipated by Maguire [U.S. Pat. Nos. 7,121,278 and 7,392,805 teaching an apparatus and method for a dual-controlled manual ventilator] and provides for a method and apparatus for performing volume-controlled and/or pressure-controlled manual ventilation. As a result, this device can address the significant disparities in patient safety between mechanical and manual ventilation, as lung-protective guideline compliance—i.e., ensuring uncontrolled breath delivery does not result in over-inflation causing VILI—is able to be provided from the very first breath during initial institution of artificial ventilation (via volume-controlled manual ventilation) until such a time as the patient can be transitioned to mechanical ventilation. Such an approach introduces a methodology for performing universal guideline-compliant ventilation throughout changeable periods of manual and mechanical modes.

As previously mentioned, artificial ventilation is initiated using a manual ventilator, with a subsequent need for a separate mechanical ventilator to enable patient transition to an automated mode most suitable for sustained support. The requirement for two separate devices—manual and mechanical—presents cost and logistical challenges. As previously described, mechanical ventilators currently in the field require financial resources that are beyond many ambulance services and hospitals in developing countries. In addition, even hospitals in advanced healthcare systems find mechanical ventilators sufficiently cost-prohibitive to make them readily available in most hospital rooms. Additionally, transport ventilators designed specifically for ambulance use and patient movement within hospitals are deemed too costly for widespread adoption.

Accordingly, one can see that it is common for patients undergoing artificial ventilation to alternate between periods of manual and mechanical ventilation, but that substantially different, separate modalities are employed for this purpose. It can also be seen that there are several care venues where patients must undergo artificial ventilation for up to an hour or more—or even days—where the financial resources needed to provide for a mechanical ventilator are often unavailable. It can also be seen that a manual ventilator must always be immediately at hand during mechanical ventilation in the event it is needed to sustain life in the event the mechanical ventilator requires maintenance, is suspected of malfunction, or fails. It is also apparent that small size is one of several practical requirements in order for a mechanical ventilator to be suitable for out-of-hospital use and for portability. Finally, significant cost, logistical and practicality barriers prevent widespread accessibility of mechanical ventilators, particularly in developing countries. Accordingly it can be seen there is an acute need for a singular, less costly, readily portable and convertible apparatus that is capable of delivering lung-protective ventilation in both manual and mechanical modes.

In accordance with the previous description, FIG. 1 depicts a preferred embodiment of a volume and/or pressure-controlled manual ventilator having an intake end, an output end, and a configurable control enabling the output volume and/or maximum pressure to be adjusted by the user. The preferred embodiment is shown with an exhalation valve and patient face mask in this presentation, suitable for use in manual mode. While the preferred embodiment is of cylindrical shape, it is to be understood that other configurations of volume and/or pressure controlled manual ventilators may be allowed, such as a rectangular-shaped ventilator, while remaining within the scope of the present invention. The preferred cylindrically-shaped embodiment of volume and/or pressure-controlled manual ventilator of FIG. 1. is configured to compress along the short axis of its shape. It is to be understood that alternative configurations of compression of the volume and/or pressure-controlled manual ventilator, such as along the long-axis, are other possibilities that remain within the scope of the present invention.

Figure 2:
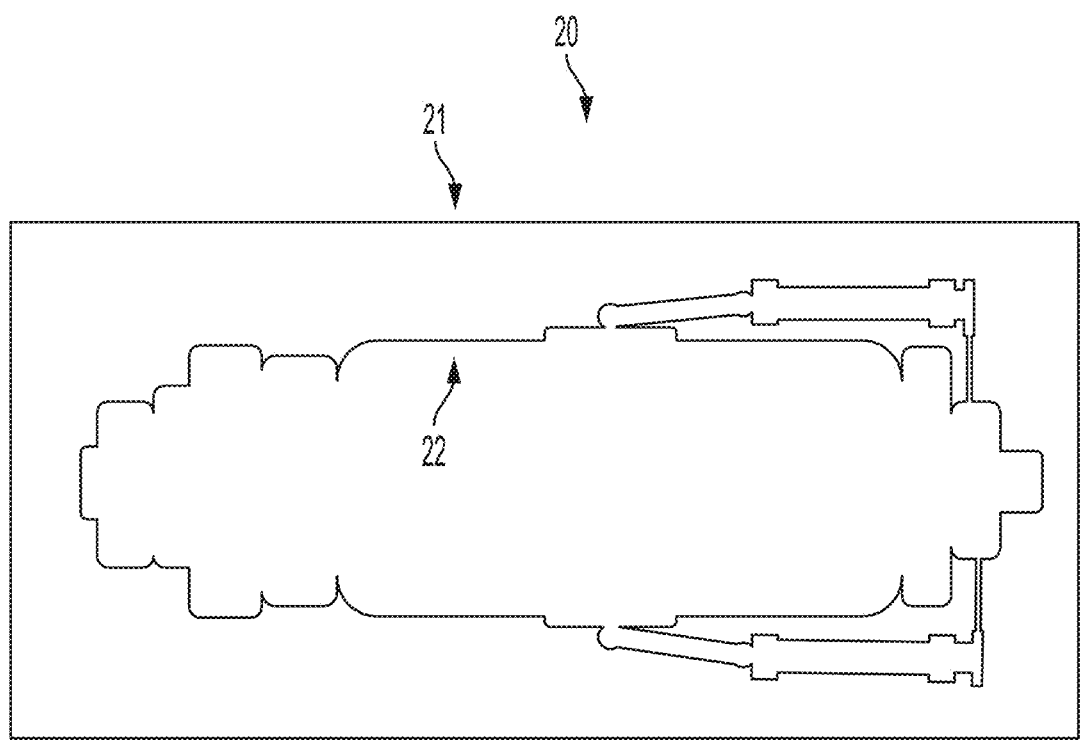
FIG. 2 is a perspective view of a storage case for the manual ventilator shown in FIG. 1, according to an embodiment of the invention.

FIG. 2 depicts a preferred embodiment of a storage case for a volume and/or pressure-controlled manual ventilator, whereby the storage case has an inner housing surface of sufficient shape and size to accommodate a volume or pressure-controlled manual ventilator, together with an outer housing surface that is preferably compact and otherwise shaped to enable placement in the immediate vicinity of the patient without undue incursions on other medical apparatus.

Figure 3:
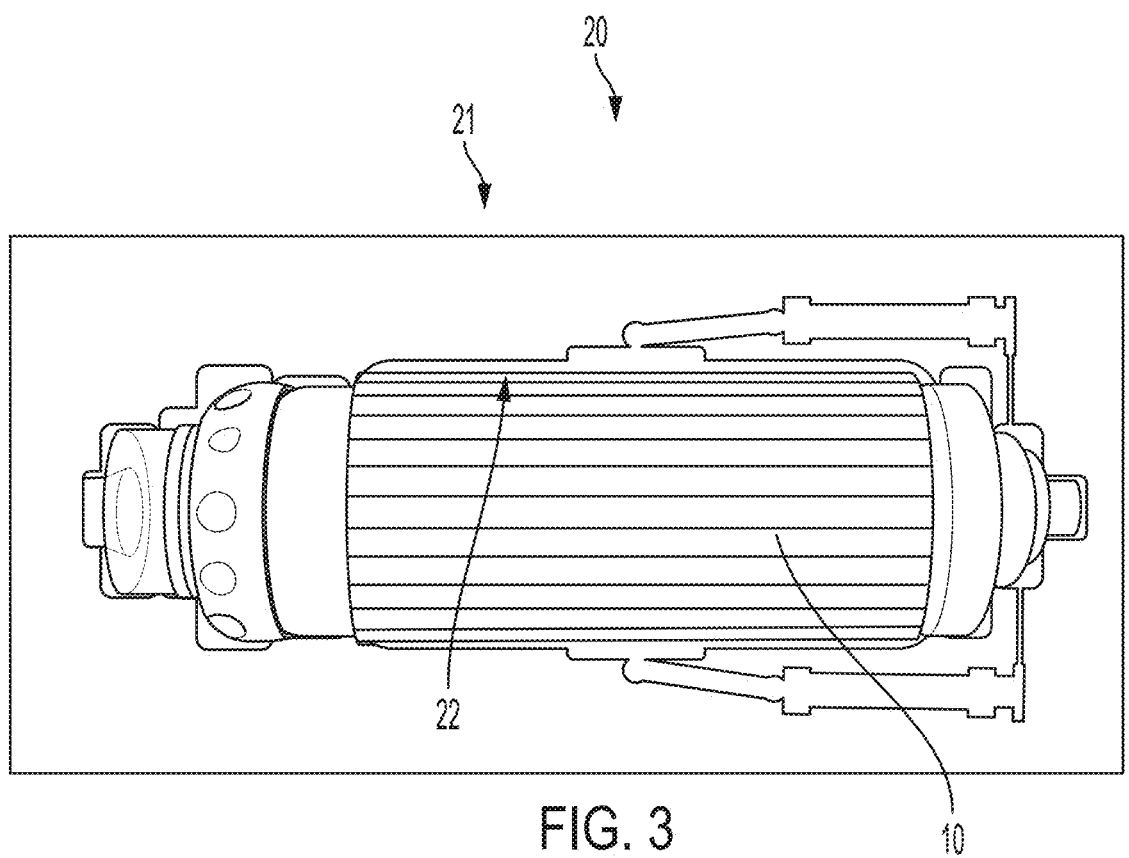
FIG. 3 is a perspective view of the storage case shown in FIG. 2 housing the manual ventilator of FIG. 1, according to an embodiment of the invention.

FIG. 3 depicts the preferred embodiment of volume and/or pressure-controlled manual ventilator of FIG. 1. placed inside the preferred embodiment of an inner housing surface of the storage case of FIG. 2., whereby the exhalation valve and patient face mask have been removed from the volume and/or pressure-controlled manual ventilator prior to installing in the unit. The inner housing surface readily accommodates the ability for insert and removal of the volume and/or pressure-controlled manual ventilator, thereby providing a means for the invention to rapidly convert between manual mode (where the volume and/or pressure-controlled manual ventilator is manually operated by a user) and mechanical mode (where the volume and/or pressure-controlled manual ventilator is mechanically actuated via actuating mechanisms contained within the storage case).

Figure 4:
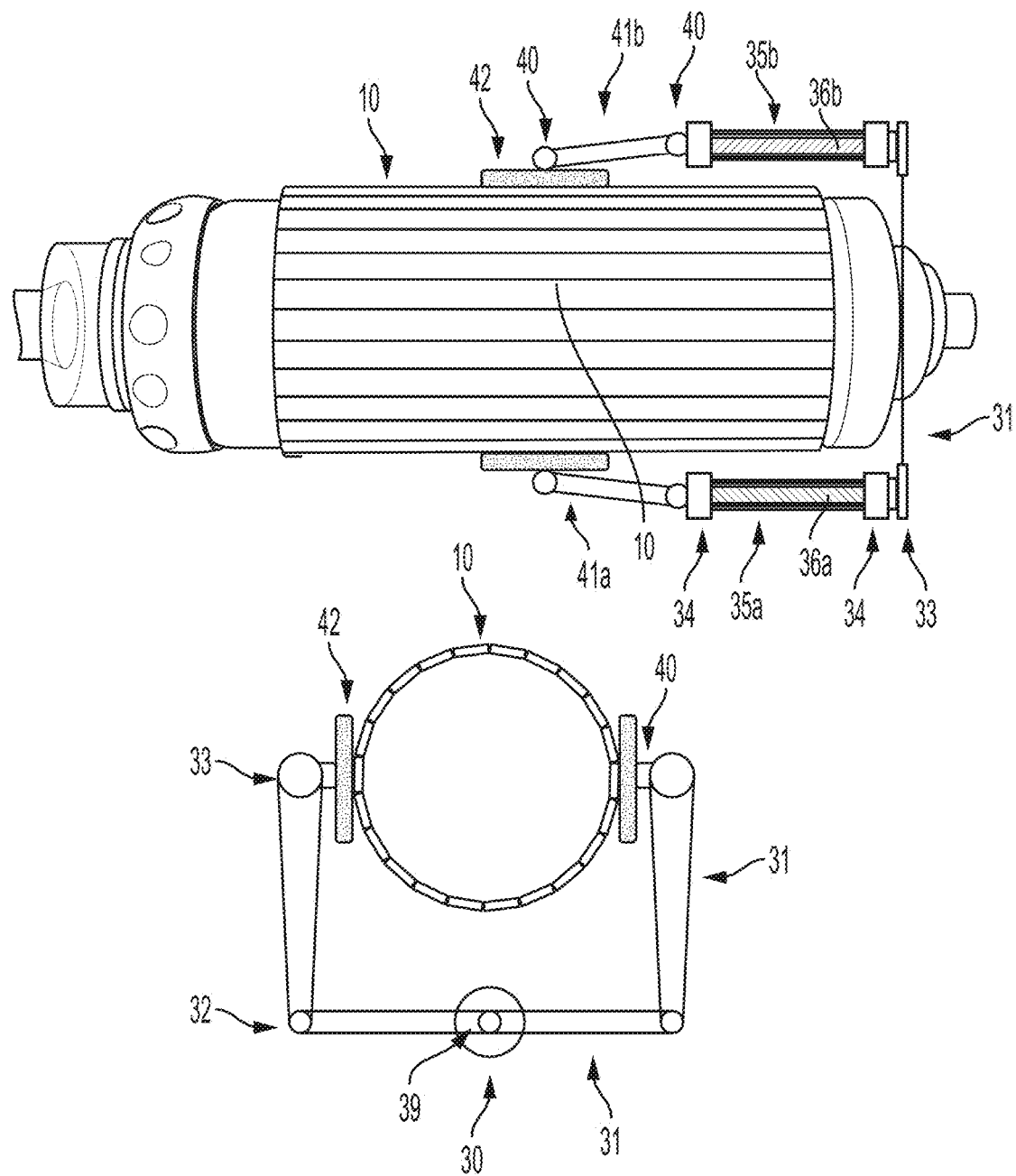
FIG. 4 is a perspective view of an actuating mechanism with the manual ventilator of FIG. 1 in a pre-breath delivery state, according to an embodiment of the invention.

FIG. 4 depicts a preferred embodiment of volume and/or pressure-controlled manual ventilator of FIG. 1 placed inside the preferred embodiment of an inner housing surface of a storage case of FIG. 2, whereby the actual housing surface is not shown in order to better portray a preferred embodiment for an actuating mechanism that is contained within the said storage housing. The actuating mechanism is portrayed in the pre-breath delivery state of operation from both long and short axis views (with long axis view shown above the short axis view in the drawing).

Figure 5:
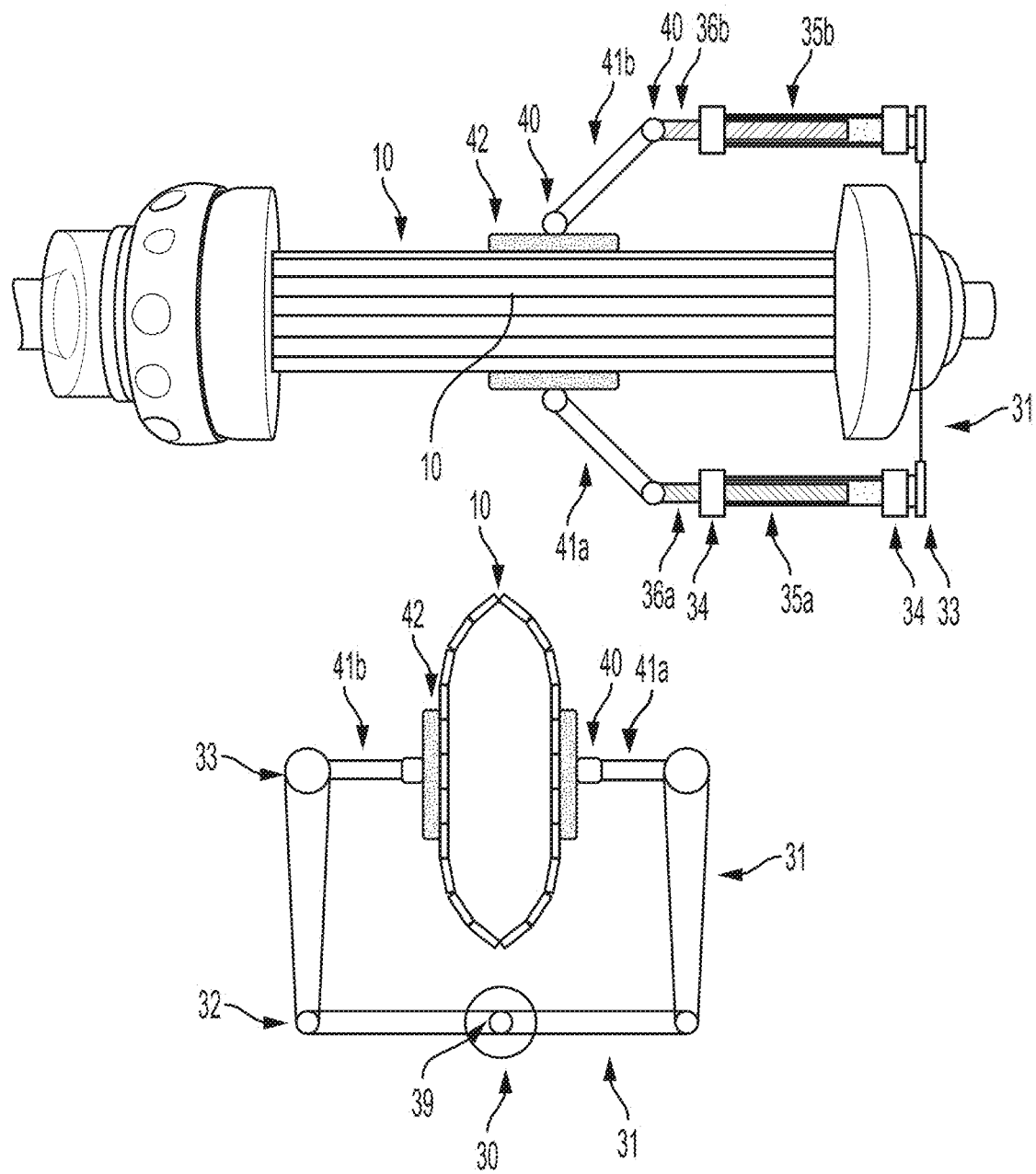
FIG. 5 is a perspective view of the actuating mechanism shown FIG. 4 with the manual ventilator of FIG. 1 in an intermediate state of partial breath delivery, according to an embodiment of the invention.
Figure 6:
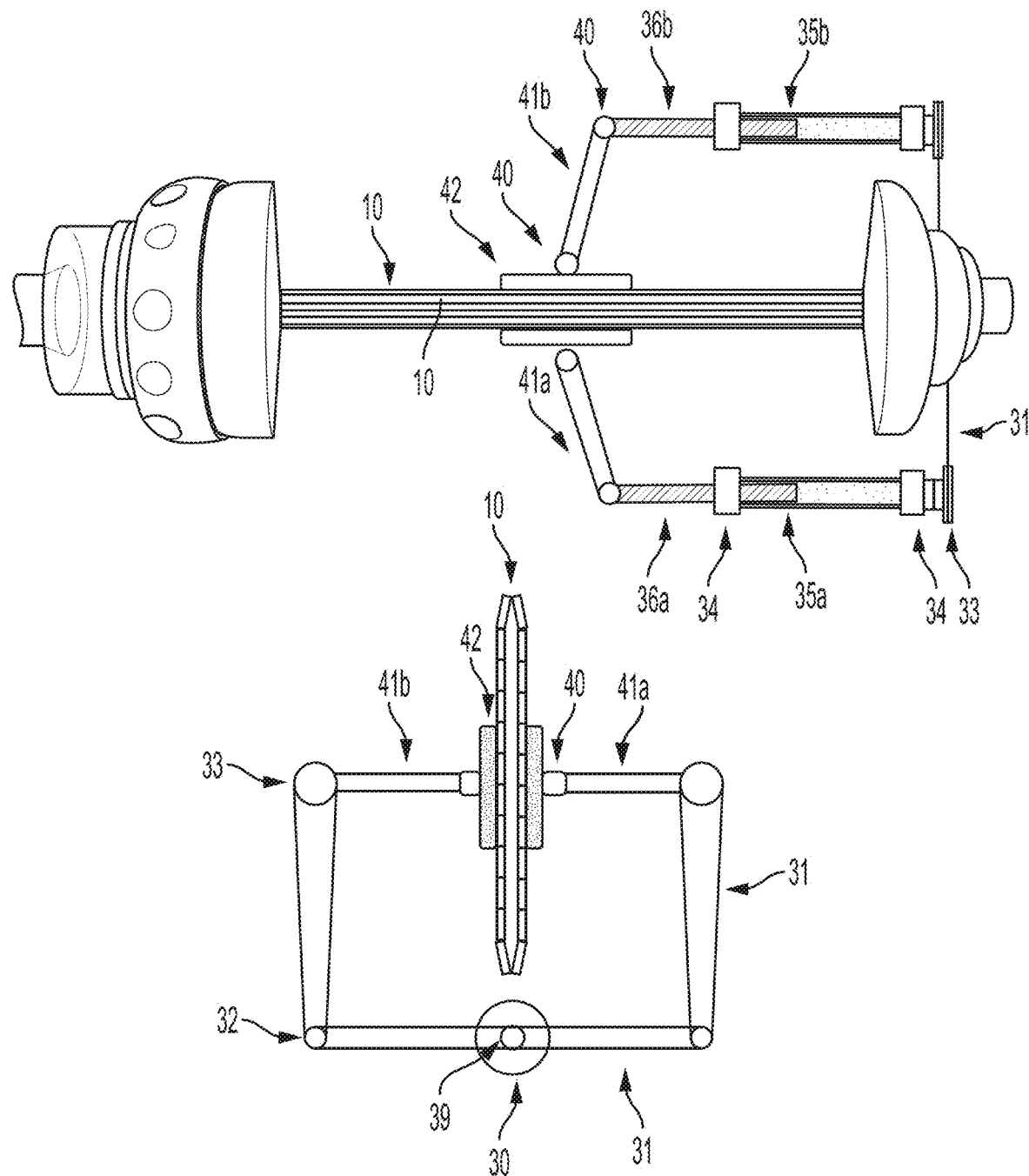
FIG. 6 is a perspective view of the actuating mechanism shown in FIGS. 4 and 5 with the manual ventilator of FIG. 1 in a complete breath delivery state, according to an embodiment of the invention.
Figure 7:
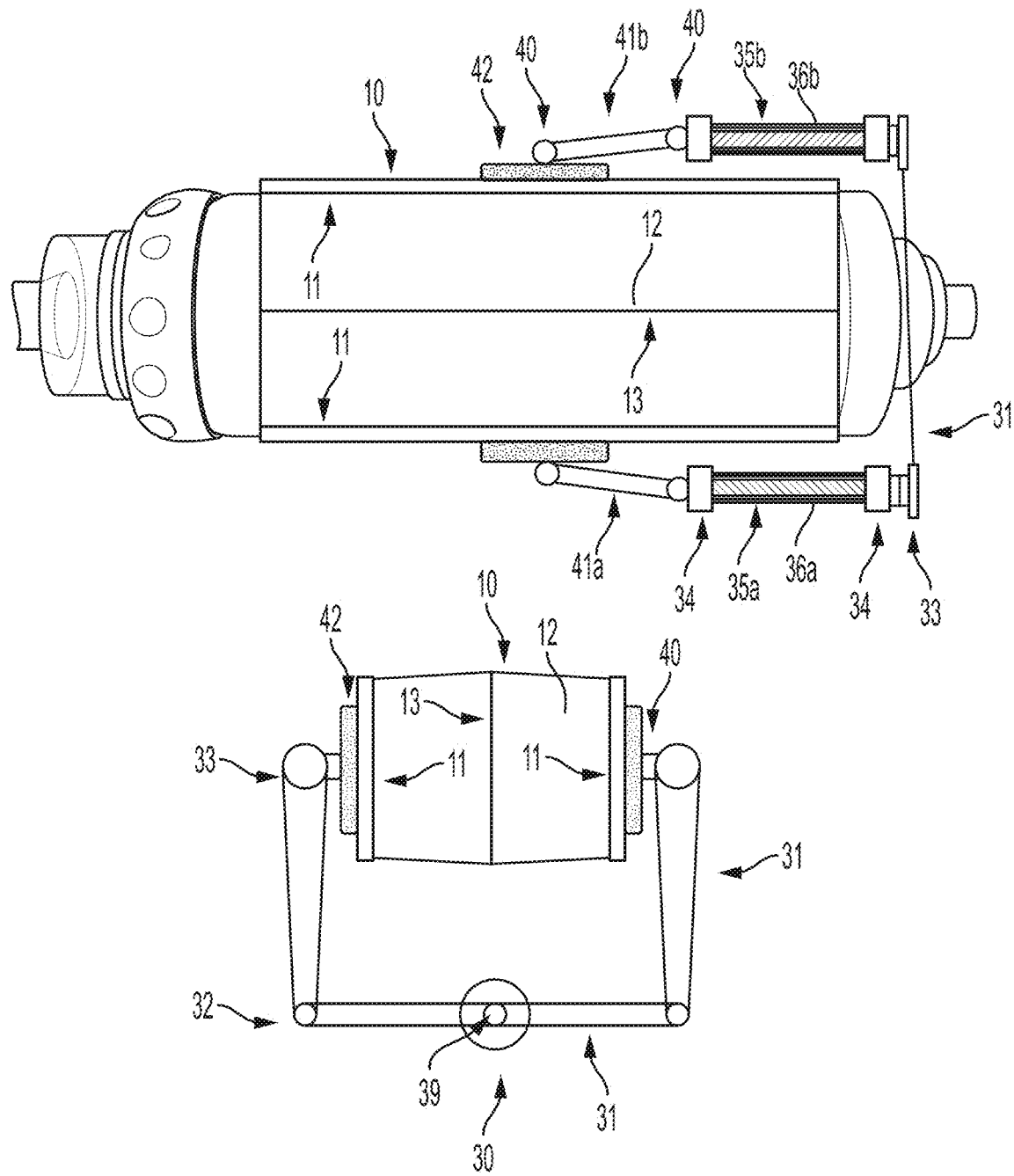
FIG. 7 is a perspective view of an actuating mechanism with a volume and/or pressure-controlled manual ventilator in a pre-breath delivery state, according to an embodiment of the invention.
Figure 8:
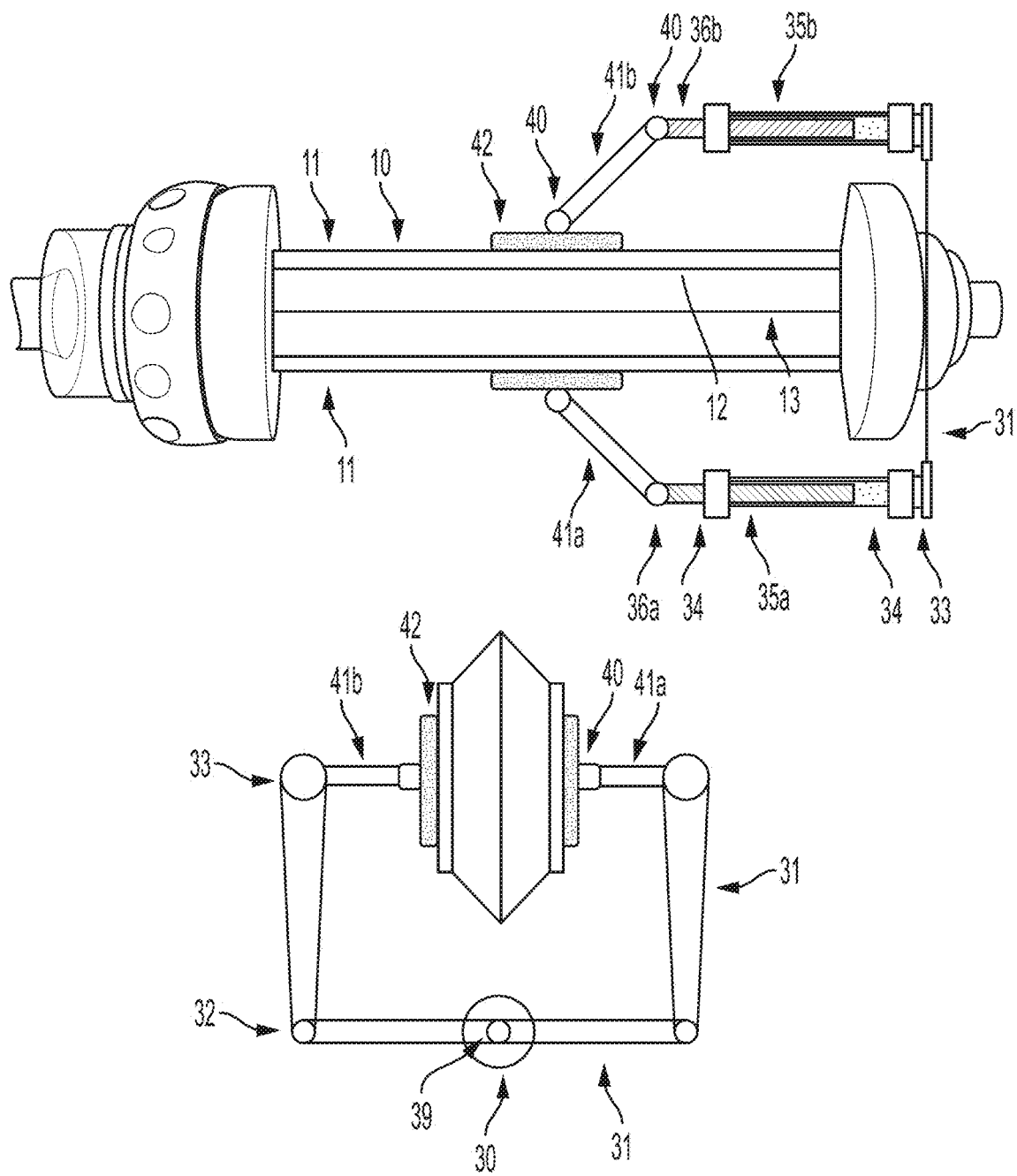
FIG. 8 is a perspective view of the actuating mechanism and manual ventilator shown in FIG. 7 in an intermediate state of partial breath delivery, according to an embodiment of the invention.
Figure 9:
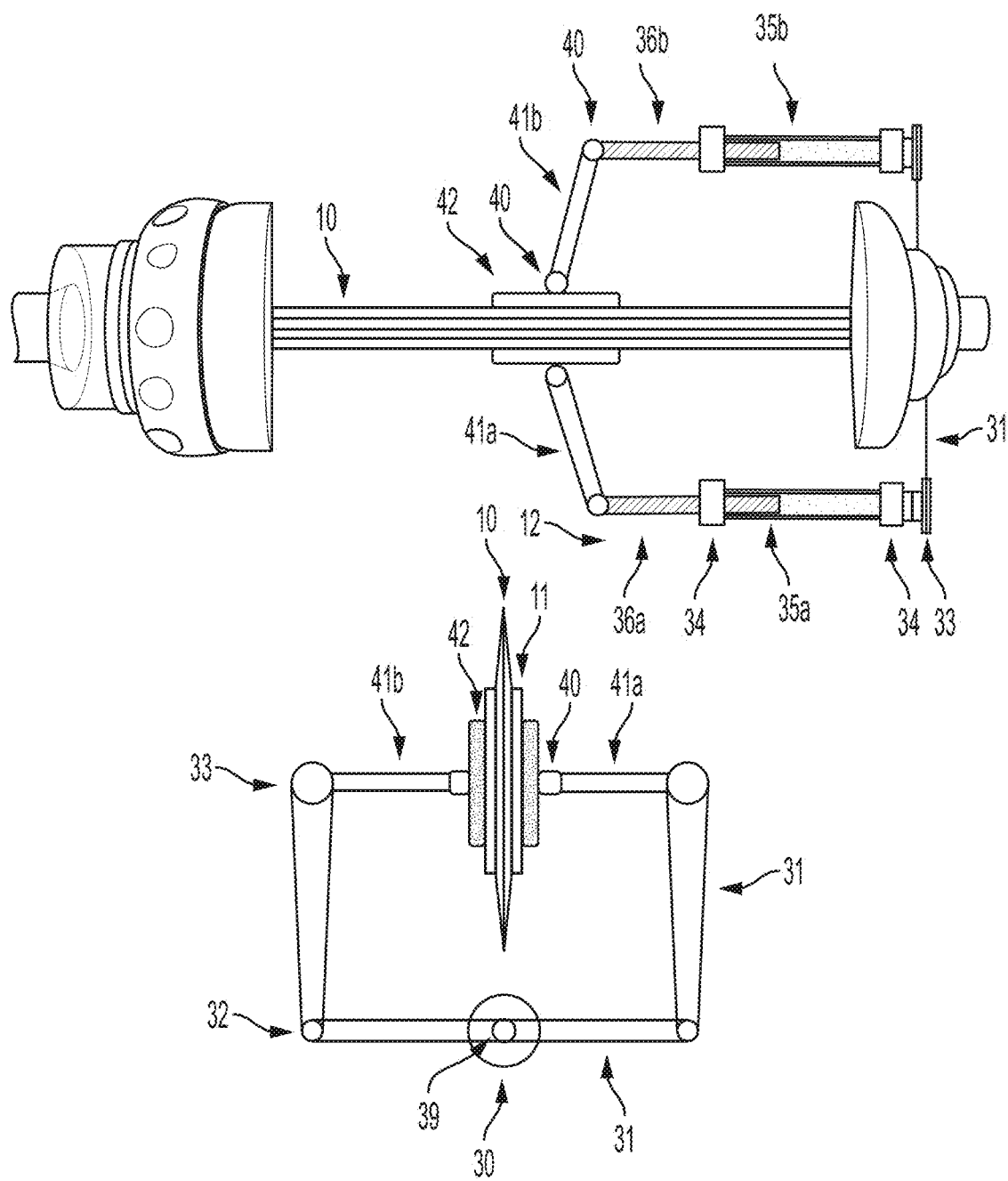
FIG. 9 is a perspective view of the actuating mechanism and manual ventilator shown in FIGS. 7 and 8 in a complete breath delivery state, according to an embodiment of the invention.

FIG. 5 shows identical components of FIG. 4, again in both long and short axis views, except the actuating mechanism is portrayed in a configuration representing an intermediate step of partial breath delivery from the convertible ventilator to the patient. This configuration also represents an intermediate step of partial ventilator re-inflation that takes place while the patient is actively exhaling after delivery of a previous breath from the convertible ventilator. FIG. 6 shows identical components of FIG. 4, also in long and short axis views, except the actuating mechanism is portrayed in a configuration representing complete breath delivery. FIGS. 7-9 depict an alternative embodiment of the invention in identical views and similar configurations as respectively shown in FIGS. 4-6.

With respect to the reference numerals in FIGS. 1-9, 10 series numerals refer to various forms and components of volume and/or pressure-controlled manual ventilator. 20 series numerals refer to various attributes of a storage case housing. 30 series numerals point to various actuating means (mechanical, electrical and/or pneumatic) in the housing that articulate with the volume and/or pressure-controlled manual ventilator to provide for operation of the volume and/or pressure-controlled manual ventilator.

40 series numerals refer to various components that may be employed to transmit articulated action from one or more power sources to 30 series actuating components. 60 series numerals point to various patient connection means suitable for use during manual, mechanical, or both modes of operation.

Finally, 90 series numerals refer to external connections of the case to electrical and/or pneumatic means, including but not limited to one or more connections to compressed air and/or oxygen sources, and/or one or more connections to electrical power sources.

Referring to FIG. 1, a preferred embodiment of a volume and/or pressure-controlled manual ventilator 10 is depicted. Manual ventilator 10 includes an output end 61, an output one-way valve assembly 62 and an input end having a one-way valve 63. When the volume and/or pressure-controlled manual ventilator 10 is manually compressed by a user, the one-way valve at the input end 63 is force closed and gas contained within the volume and/or pressure-controlled manual ventilator 10 is directed toward the output end 61. In the depicted configuration, gas output is further directed through the output one-way valve assembly 62 to an output connector 65 capable of being connected to a patient interface means such as a face mask 66 or alternatively an airway tube (not shown).

After delivery of a breath, removal of compression effort on the volume and/or pressure-controlled manual ventilator 10 results in the output one-way valve 62 closing, thereby preventing exhaled gas from the patient entering the volume and/or pressure-controlled manual ventilator 10. At the same time, in the event the volume and/or pressure-controlled manual ventilator 10 is of the self-inflating type, the elasticity and/or memory function of the unit causes it to re-expand, creating a vacuum that causes the intake one-way valve 63 to open, thereby providing a gas source to facilitate re-inflation of the volume and/or pressure-controlled manual ventilator 10. Alternatively, in the event the volume and/or pressure-controlled manual ventilator is of the flow-inflating type, then the flow source connected to the intake one-way valve 63 forces it open, thereby facilitating re-inflation of the volume and/or pressure-controlled manual ventilator 10 under the operating pressure of the flow source.

When used in manual mode, the volume and/or pressure-controlled manual ventilator 10 can be fitted with a pressure-relief valve 64 providing for maintenance of a minimum positive pressure against the patient output 66, whereby this constitutes a means to achieve positive end expiratory pressure (PEEP).

In the preferred embodiment of the present invention, the output one-way valve assembly 62, pressure-relief valve 64, output connector 65 and patient interface 66 can be readily and rapidly removed as a single assembly to prepare the volume and/or pressure-controlled manual ventilator 10 for placement into the storage case (not shown in FIG. 1) as a preparatory step prior to converting from manual to mechanical mode.

FIG. 2 shows a storage case 20 having an outer housing surface 21 and inner housing surface 22. The outer housing surface 21 is preferably designed to minimize outer dimensions to facilitate maximal portability, and may have one or more external connections in any configuration (obviating depiction of any specific configuration in FIG. 2) to enable connection to one or more sources of compressed air and/or oxygen (or other compressed gas sources for purposes to include utilization as a power source), one or more electrical connections (such as to an internal and/or external battery pack, and/or a wired electrical power source), one or more wired and/or fiber-optic or other optical connections for purposes of information exchange and/or connection to a control means.

FIG. 2 also demonstrates how the inner surface 22 of the storage case may be designed to cradle a volume and/or pressure-controlled manual ventilator. Further, the inner surface 22 may provide one or more anchoring points for actuating mechanism components, including one or more grooves specifically configured to direct movement of one or more articulated components of an actuating mechanism.

FIG. 3 depicts the preferred embodiment of the volume and/or pressure-controlled manual ventilator 10 of FIG. 1 positioned within the inner surface 22 of the storage case 20. It can be seen that the outer surface 21 of the storage case 20 is not substantially larger than the preferred embodiment of the volume and/or pressure-controlled manual ventilator 10, thereby constituting a compact apparatus.

FIG. 4 shows the preferred embodiment of the volume and/or pressure-controlled manual ventilator 10, and components of a preferred version of an actuating mechanism resulting in the ability for the invention to operate in mechanical mode. The upper drawing of FIG. 4. shows a long axis view, while the lower drawing of FIG. 4. depicts the same components and configuration of the upper drawing (to the extent they are visible). Noting the symmetry of the invention, labeling pointing to components on one side of each of the drawings also refers to the visually identical component on the opposite side. The actuating mechanism is primarily driven by a power unit 30, which could comprise an electrical servo-type motor, or a comparable adjunct capable of operating from a pneumatic and/or hydraulic means. The power unit 30 is preferably fitted with a dual-channel pulley 39 capable of transmitting rotational force to one or more belts or chains 31. The belts or chains 31 can be connected directly to receiving pulleys 33 that are connected to a linear rod mechanism 35+36 comprising an outer housing 35 and inner rod 36 that converts the rotating motion of the power unit 30 into fore- and aft or axial movement of the linear rod mechanism. Alternatively, the belts or chains 31 can be indirectly connected to the receiving pulleys 33 by means of one or more transmission pulleys 32 to permit flexibility in relative positioning of the power unit 30 relative to the linear rod mechanism. The relative sizes of the power unit pulley 39, receiving pulleys 33 and, if present, one or more transmission pulleys 32 can be provided in such a way to optimize torque, precision and rotational speeds of the actuating mechanism to be most suitable to the application of volume and/or pressure controlled mechanical ventilation.

In the preferred variation depicted in FIG. 5, once rotational motion is transmitted to the receiving pulleys 33, it is directly transmitted to the linear rod mechanism outer housing 35 such that it is forced to rotate. The linear rod mechanism outer housing 35 is maintained in a fixed physical position without any encumbrances on rotational movement transmitted by the receiving pulleys 33, with this being provided for in this preferred embodiment by one or more bearings 34. The linear rod mechanism outer housing 35 is preferably fitted with a threading pattern that mates with an opposing threading pattern of the inner rod 36, whereby rotation of the linear rod mechanism outer housing 35 relative to rotational inaction of the linear rod 36 will cause the latter to move in a substantively fore-and-aft motion relative to the linear rod mechanism outer housing 35. Thread pitch patterns of the linear rod mechanism outer housing 35 and linear rod 36 can be configured to optimize torque, precision and rotational speeds of the actuating mechanism to be most suitable to the application of volume and/or pressure controlled mechanical ventilation.

The inner rod 36 of the linear rod mechanism is connected to an applicator pad 42 that is positioned to apply direct pressure to the outside of the volume and/or pressure-controlled manual ventilator 10 such that the linear rod mechanism 35+36 effectively controls the inflation and deflation of the volume and/or pressure-controlled manual ventilator 10. This can be achieved directly by configuring the linear rod mechanism 35+36 parallel to the movement of the applicator pad 42 required to compress the volume and/or pressure-controlled manual ventilator 10. However, in order to provide for a more compact overall configuration of the preferred embodiment, the linear rod mechanism 35+36 is configured perpendicular to the movement of the applicator pad 42 required to compress the volume and/or pressure-controlled manual ventilator 10. This results in linear rod 36 being connected to a transmission rod 41 having one or more hinges 40, with the hinges 40 being restricted to movement on a single plane such that the movement of the linear rod 36 together with the transmission rod 41 results in a sufficient redirection of the actuating movement to result in movement of the applicator pad 42 in such a way as it causes compression of the volume and/or pressure-controlled manual ventilator 10. The length and other attributes of the transmission rod 41 relative to the movement of the inner rod 36 and applicator pad 42 can be provided in such a way to optimize torque, precision and rotational speeds of the actuating mechanism to be most suitable to the application of volume and/or pressure controlled mechanical ventilation.

Accordingly, the configuration of the components as shown in FIG. 4 can be seen to show the volume and/or pressure-controlled manual ventilator 10 to be fully inflated and prepared to deliver a breath to the patient.

FIG. 5 contains the same components of FIG. 4, except it can be seen that actuation of the power unit 30 has caused the belts or chains 31 to transmit rotational force to the receiving pulleys 33 such that extension of the inner rods 36 have caused the applicator pads 42 to compress the volume and/or pressure-controlled manual ventilator 10. It can also be seen how the preferred embodiment of the volume-control manual ventilator as described by Maguire [U.S. Pat. Nos. 7,121,278 and 7,392,805] result in volume-control being achievable via the principal mechanism inherent to the volume and/or pressure-controlled manual ventilator 10, such that the configuration of the apparatus in FIG. 5 (and FIG. 8) may also represent delivery of a full breath if the volume and/or pressure-controlled manual ventilator 10 is set to a breath size less than the maximum capable to be delivered by the volume and/or pressure-controlled manual ventilator. The configuration of the apparatus in FIG. 5 also represents partial re-inflation with the actuating mechanism operating in reverse, which is provided by reversing the direction of the motor unit 30. Reverse motion can alternatively be provided through various intuitive embodiments such as a reverse gear clutching mechanism or other means.

FIG. 6 contains the same components of FIGS. 4 and 5, except it can be seen that further actuation of the power unit 30 has caused the actuating mechanism to fully depress the volume and/or pressure-controlled manual ventilator 10. This configuration represents delivery of the maximum breath volume possible in the event the volume and/or pressure-controlled manual ventilator is set to allow delivery of its maximal breath size.

Several control elements are provided for user control of the rotational motion of motor unit 30, such as, but not limited to, the direction and/or rotational speed to be configurable by the user. Such control can be provided through a logic circuit, microprocessor(s) and/or other control means common in the art of control of rotational movement.

Another control element in the present invention could be actuation of an external exhalation valve contained in a breathing circuit connecting a mechanical ventilator to a patient. These are typical in the field and allow gases from patient exhalation to be directed to a tube circuit that is separate from that used for delivery of inhalation gases. Such exhalation valves can be pneumatically or electrically operated.

Several sensing elements common in the art of linear movement and/or pressure detection and/or electrical impedance are also provided for feedback to the user and/or a logic circuit and/or microprocessor(s) interfaced with the motor unit 30 and/or other elements of the invention. For example, a pressure sensor can be fitted to the output end 61, either side of the output one-way valve assembly 62, either side of the input one-way valve assembly 63, and/or elsewhere in the invention to enable pressure measurements in various locations throughout the invention to be utilized for user feedback and/or as input data able to be utilized by logic circuits, microprocessor(s) and/or other sensing and/or control means.

Several sensing elements specific to an electrically-operated motor serving as the power unit 30 are common to the art of feedback and control of electrical motors. Sensors providing real-time data regarding the rotation position of the motor can enable derivative calculation of rotational speed through calculation of change in rotational position over a specific unit of time. Rotational acceleration can be calculated through serial calculations of rotational speed over time. Exemplary examples of sensors known in the art include resolvers, encoders, and/or sensors working off Hall Effect means.

The embodiments as described are to be understood as merely exemplary, with the invention not limited to the version described and encompassing all materially equivalent versions. For example, FIGS. 7-9 show an alternative embodiment of a volume and/or pressure-controlled manual ventilator 10 in identical configurations and views as respectively shown in FIGS. 4-6, whereby the alternative embodiment of volume and/or pressure-controlled manual ventilator 10 has opposing squeezing surfaces 11 and a rigid collapsible gas container 12 having one or more creases 13 to facilitate collapse of the gas chamber 12 when compressed manually and/or by applicator pads 42. Other embodiments of volume and/or pressure-controlled manual ventilator 10 capable of being used either manually or mechanically can be intuitively derived from the present invention.

Alternative embodiments and/or placement of the power unit 30 shown in FIGS. 4-9 can also be intuitively derived from the present invention. For example, in place of transmission pulleys 32 and belts or chains 31 as a means to ensure synchronized movement of transmission rods 41 and applicator pads 42, two power units 30 can be directly interfaced to receiving pulleys 33 and controlled by a logic circuit or other control means providing synchronized movement.

Alternative embodiments of the linear rod mechanism 35+36 shown in FIGS. 4-9 can also be intuitively derived from the present invention. Hydraulic and/or electromagnetic actuators can be substituted for the linear rod mechanism 35+36, thereby providing direct action on transmission rods 41 and applicator pads 42, with synchronized movement of hydraulic and/or electromagnetic actuators being provided for through a logic circuit or other control means providing synchronized movement. This embodiment could obviate the need for transmission pulleys 32 and belts or chains 31.

Another alternative embodiment of the linear rod mechanism 35+36 can be intuitively derived from the present invention that eliminates the need for transmission rods 41 by mounting the linear rod mechanism 35+36 in alignment with the intended movement of the applicator pads 42. This can be achieved either through intuitive reconfiguration of transmission pulleys 32 and belts or chains 31 relative to the power unit 30, or through one of the alternative embodiments providing for a logic circuit or other control means providing synchronized movement of the linear rod mechanism 35+36 and actuating pads 42.

Finally, another alternative embodiment for converting the rotating motion of the power unit 30 into fore- and aft movement of the linear rod mechanism 35+36 can be intuitively derived from the present invention through use of one or more shafts that may be fitted with a series of one or more sprockets and/or universal joints and/or other means allowing for the connected shafts to assume a configuration suitable for transmitting the rotational motion of the power unit 30 to the linear rod mechanism 35+36.

Figure 10:
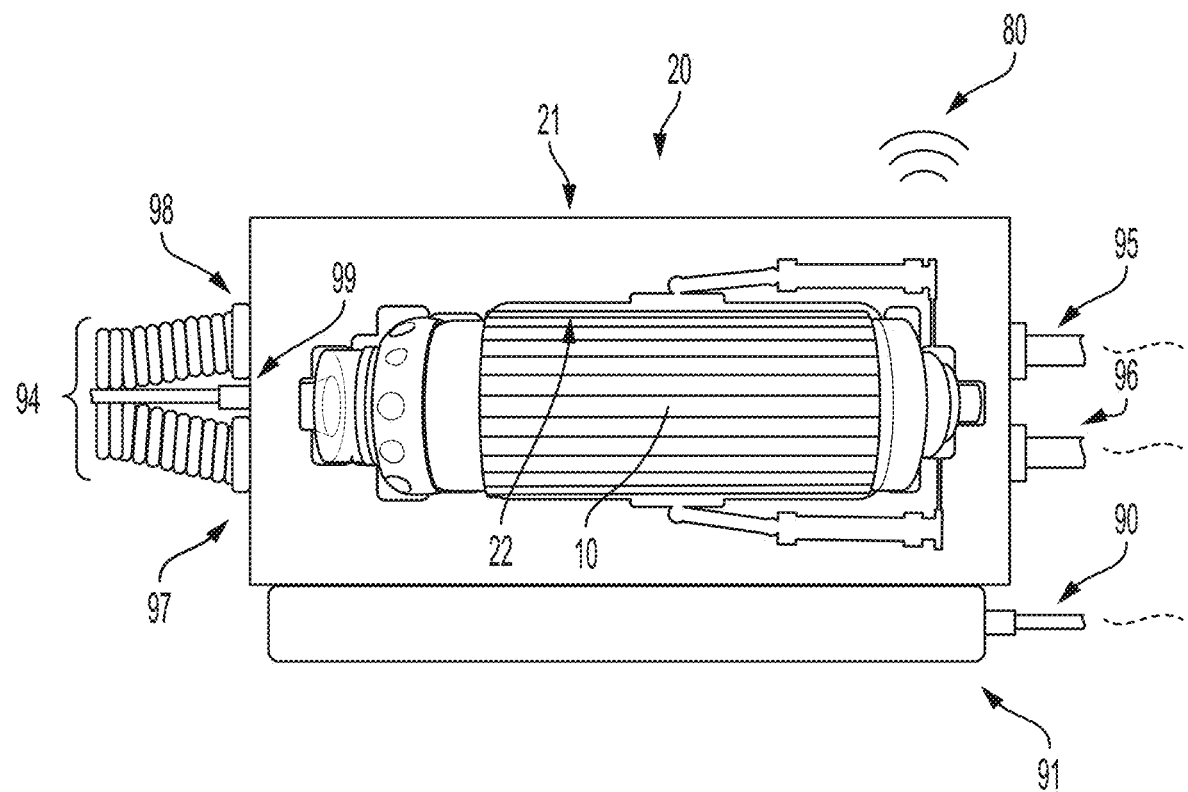
FIG. 10 is a perspective view of a storage case housing a volume and/or pressure-controlled manual ventilator during administration to a patient, according to an embodiment of the invention.
Figure 10:
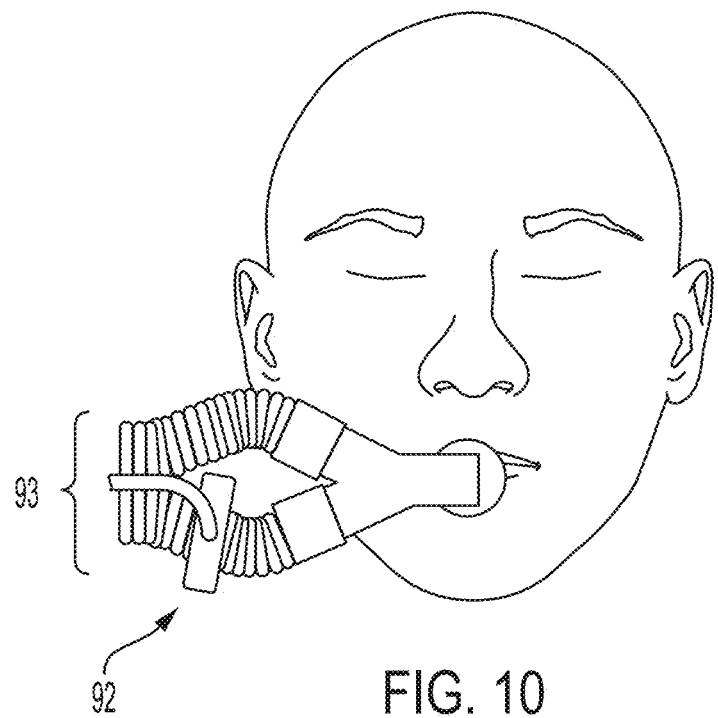

FIG. 10 refers to a preferred embodiment of the storage case 20 containing a volume and/or pressure-controlled manual ventilator 10, illustrating examples of various specific external connections. An external compressed oxygen connection 95 and external compressed air connection 96 are provided in order to enable the invention to draw in respiratory gases for subsequent administration to a patient. Alternatively, or in addition, a separate connection can be provided for use of anesthetic gases. Connections for a ventilator circuit 93+94 typical to the art of providing mechanical ventilation are also provided. A ventilator circuit inhalation connection 97 enables the invention to deliver inhalation gas to the patient via the ventilator circuit. A ventilator circuit exhalation connection 98 enables the invention to receive exhalation gas from the patient. An external exhalation valve controlling tube/wire 99 enables the invention to actively close an exhalation valve 92 located near the patient connection that prevents inspiratory gases from bypassing the patient when a breath is being delivered. This external exhalation valve can also be located immediately adjacent to the ventilator circuit exhalation connection 98, enabling a shorter exhalation valve controlling tube/wire 99.

With attributes of the apparatus being adequately described, various methodologies of performing mechanical ventilation will now be provided referring to the drawings as previously described.

The most important attribute of artificial ventilation is tidal volume—the amount of inspiratory gas delivered to each patient during each breath. This invention provides for control of tidal volume via the volume and/or pressure-controlled manual ventilator 10 at its core. When being directly compressed by a user's effort during manual mode, the volume and/or pressure-controlled manual ventilator stops allowing further delivery of additional inspiratory volume once the preset maximum is reached. The user then manually relaxes compression, enabling the unit to re-expand in preparation for delivery of the next breath. To provide for this same function during mechanical mode, whereby the volume and/or pressure-controlled manual ventilator 10 is compressed through action of the motor unit 30 (or other alternative means as previously described), it is possible to utilize a sensing and control means as a feedback loop to program a logic circuit, microprocessor(s) or other control means to have a maximum power setting that is greater than the resistance needed to generate sufficient effort to inflate the patient's lungs under positive pressure, but less than the power setting that would be sufficient to result in destruction of the volume and/or pressure-controlled manual ventilator 10. This can be coupled with a sensing means that then enables the logic circuit and/or microprocessor(s) to detect full delivery of the preset tidal volume selected on the volume and/or pressure-controlled manual ventilator 10, such that the logic circuit and/or microprocessor(s) then trigger reverse motion of the motor unit 30 to enable re-expansion of the volume and/or pressure-controlled manual ventilator 10 in preparation for delivery of the next breath.

Whenever a breath is mechanically delivered, note that compression of the volume and/or pressure-controlled manual ventilator 10 by the applicator pads 42 will cause an increase in pressure inside the volume and/or pressure-controlled manual ventilator 10 causing the input one-way valve assembly 63 to close, thereby resulting in forward propulsion of breathing gas toward the output end 61, through a patent output one-way valve assembly 62 and into the ventilator circuit 94 via the ventilator circuit inhalation connection 97. To prevent breathing gas intended for the patient from bypassing the patient and directly entering the exhalation tube of the circuit and looping back to the ventilator, a control means will actively close the external exhalation valve 92 via the external exhalation valve controlling tube/wire 99. Various control means can be provided during active compression of the volume and/or pressure-controlled manual ventilator 10 as provided by the motor unit 30 or other alternative embodiments as previously described. The rotational speed of the motor unit 30 can be programmed for quick acceleration from zero rotational movement to that rotational velocity required to cause active compression of the volume and/or pressure-controlled manual ventilator 10 over a preferred period of time (for example, one second). The rotational speed of the motor unit 30 can alternatively be programmed for progressive acceleration from zero rotational movement to that rotational velocity required to cause active compression of the volume and/or pressure-controlled manual ventilator 10 over a longer period of time (for example, two seconds). This demonstrates a direct relationship between the rotational speed of the motor unit 30 with compression of the volume and/or pressure-controlled manual ventilator 10, thereby generating forward gas flow to the patient under a controllable means. Flow rate to the patient can be increased by higher rotational velocities of the motor unit 30, serving to deliver a breath of a given volume over a shorter period of time relative to the same breath volume delivered under a slower rotational velocity of the motor unit 30.

The ability to time the duration of patient inhalation as described provides effective control over both the time for inhalation (or "I-time") and, by controlling the interval between each delivered breath, what is therefore the pause between breaths during which exhalation occurs (or "E-time"). This also enables definitive control over the number of breaths delivered per minute during mechanical ventilation. For example, if I-time is configured to be two seconds and a four second pause (E-time) is provided between each breath, then one complete inhalation and exhalation cycle will be six seconds in length, corresponding to ten breath cycles delivered per minute. Additionally, it is typical in the field to often refer to the ratio between I-time and E-time; in this example the I:E ratio is two to four, reduced to one to two as expressed as a ratio. Accordingly, the present invention is able to easily accommodate control settings to include inspiratory flow, I:E ratio, I-time, and ventilation rate.

After breath delivery, it can be noted that the breath will be sustained (or "held") by the patient until a control means causes deactivation of the external exhalation valve controlling tube/wire 99. Retrograde flow from the patient to the ventilator via the ventilator circuit inhalation connection 97 is prevented by the output one-way valve assembly 62 or a one-way valve assembly integrated in the output end 61 of the volume and/or pressure-controlled manual ventilator 10. Accordingly, a pause can be programmed between breath delivery to the patient and deactivation of the external exhalation valve.

Several additional parameters of ventilation delivery can be provided for in the present invention. For example, it is possible for the invention to provide continuous positive airway pressure (CPAP) without actively delivering any mechanically-delivered breaths by regulating pressure received by the external compressed oxygen connection 95 and/or external compressed air connection 96 and through application of a back pressure means on the ventilator circuit exhalation connection 98. This constant pressure can help reduce the work of breathing of a patient breathing on their own either to maintain or rebuild strength of respiratory muscles.

Another important feature is positive end-expiratory pressure (PEEP) that is similar to CPAP in that a specified positive pressure is always maintained in both tubes of the ventilator circuit, except PEEP refers to a non-breathing patient whereby ventilations are delivered by the volume and/or pressure-controlled manual ventilator 10 as driven by the power unit 30.

Figure 11:
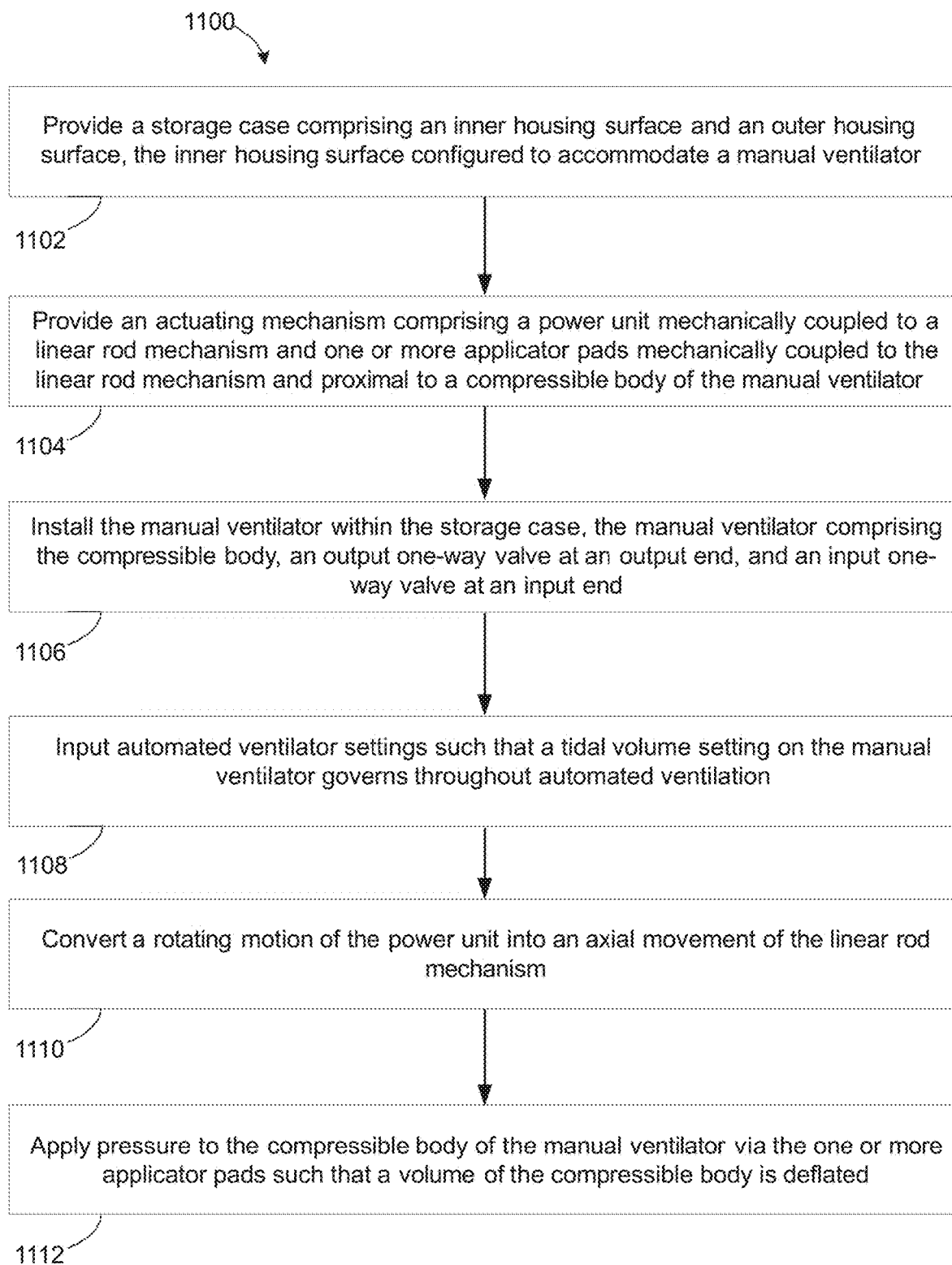
FIG. 11 is a flow diagram of method steps for actuating a volume and/or pressure-controlled manual ventilator, according to an embodiment of the invention.

Referring to FIG. 11, a process 1100 for actuating a volume and/or pressure-controlled manual ventilator 10 is illustrated. The process 1100 begins by providing a storage case 20 including an inner housing surface 22 and an outer housing surface 21 in step 1102. The inner housing surface 22 is configured to accommodate a manual ventilator 10. In some embodiments, the inner housing surface 22 of the storage case 20 includes one or more anchoring points for an actuating mechanism.

Process 1100 continues by providing the actuating mechanism including a power unit 30 mechanically coupled to a linear rod mechanism and one or more applicator pads 42 mechanically coupled to the linear rod mechanism and proximal to a compressible body of the manual ventilator 10 in step 1104. For example, in some embodiments, the power unit 30 includes an electrical servo-type motor. In some embodiments, the power unit 30 is fitted with a dual-channel pulley 39 configured to transmit rotational force to one or more belt or chains 31. In some embodiments, the linear rod mechanism is mechanically coupled to the one or more belt or chains 31 via one or more receiving pulleys 33.

In some embodiments, the linear rod mechanism includes a first outer housing 35a mechanically coupled to a first inner rod 36a and a second outer housing 35b mechanically coupled to a second inner rod 36b. For example, in some embodiments, a first of the one or more applicator pads 42 is mechanically coupled to the first inner rod 36a and a second of the one or more applicator pads 42 is mechanically coupled to the second inner rod 36b. In some embodiments, the first of the one or more applicator pads 42 is mechanically coupled to the first inner rod 36a via a first transmission rod 41a and the second of the one or more applicator pads 42 is mechanically coupled to the second inner rod 36b via a second transmission rod 41b.

Process 1100 continues by installing the manual ventilator 10 within the storage case 20 in step 1106. The manual ventilator 10 including the compressible body, an output one-way valve 62 at an output end, and an input one-way valve 63 at an input end. In some embodiments, the manual ventilator 10 includes an output connector 65 communicatively coupled to the output one-way valve 62. In some embodiments, the output connector 65 is configured to be coupled to a patient interface 66. In some embodiments, the manual ventilator 10 includes a pressure-relief valve 64 proximal the output end.

Process 1100 continues by inputting automated ventilation settings into the logic circuit and/or microprocessor in step 1108. The automated ventilation settings include I-time and rate (or I:E ratio and rate), among other settings to include tidal volume, such that, if the manual ventilator 10 is of the volume-controlled type, a duplicative tidal volume setting need not be input into the logic circuit and/or microprocessor, and the tidal volume setting on the manual ventilator will govern during automated ventilation.

Process 1100 continues by converting, by the actuating mechanism, a rotating motion of the power unit 30 into an axial movement of the linear rod mechanism in step 1110. Process 1100 finishes by applying, by the actuating mechanism, pressure to the compressible body of the manual ventilator 10 via the one or more applicator pads 42 such that a volume of the compressible body of the manual ventilator 10 is deflated in step 1112.

Figure 12:
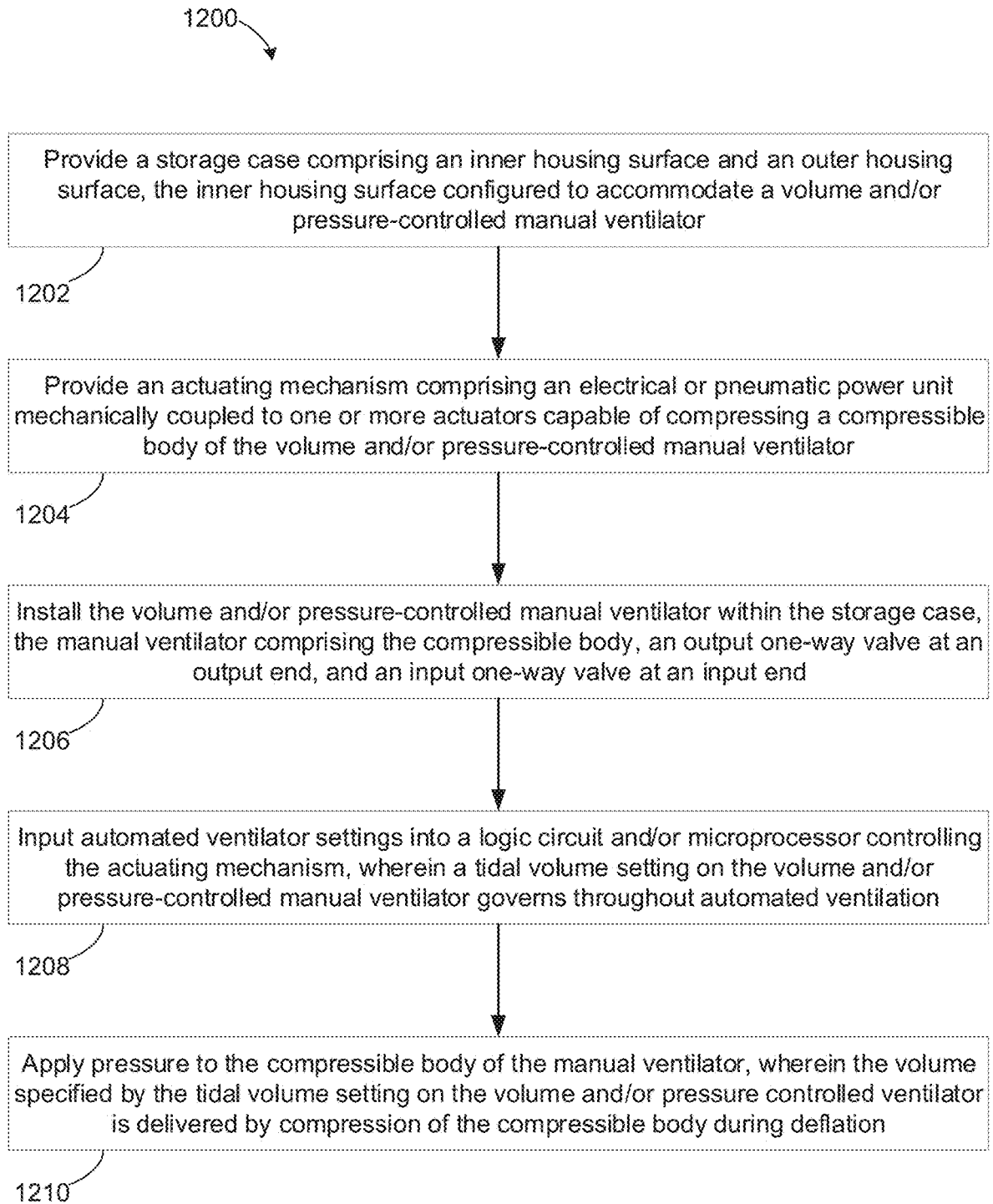
FIG. 12 is a flow diagram of method steps for actuating a volume and/or pressure-controlled manual ventilator, according to an embodiment of the invention.

Referring to FIG. 12, a process 1200 for actuating a volume and/or pressure-controlled manual ventilator 10 is illustrated. The process 1200 begins by providing a storage case 20 including an inner housing surface 22 and an outer housing surface 21 in step 1202. The inner housing surface 22 is configured to accommodate a volume and/or pressure-controlled manual ventilator 10. In some embodiments, the inner housing surface 22 of the storage case 20 includes one or more anchoring points for an actuating mechanism.

Process 1200 continues by providing an actuating mechanism including an electrical or pneumatic power unit that is mechanically coupled to one or more actuators capable of compressing a compressible body of the volume and/or pressure-controlled manual ventilator 10 in step 1204. In some embodiments, the actuating mechanism includes a power unit 30 mechanically coupled to a linear rod mechanism and one or more applicator pads 42 mechanically coupled to the linear rod mechanism and proximal to a compressible body of the manual ventilator 10. For example, in some embodiments, the power unit 30 includes an electrical servo-type motor. In some embodiments, the power unit 30 is fitted with a dual-channel pulley 39 configured to transmit rotational force to one or more belt or chains 31. In some embodiments, the linear rod mechanism is mechanically coupled to the one or more belt or chains 31 via one or more receiving pulleys 33.

In some embodiments, the linear rod mechanism includes a first outer housing 35a mechanically coupled to a first inner rod 36a and a second outer housing 35b mechanically coupled to a second inner rod 36b. For example, in some embodiments, a first of the one or more applicator pads 42 is mechanically coupled to the first inner rod 36a and a second of the one or more applicator pads 42 is mechanically coupled to the second inner rod 36b. In some embodiments, the first of the one or more applicator pads 42 is mechanically coupled to the first inner rod 36a via a first transmission rod 41a and the second of the one or more applicator pads 42 is mechanically coupled to the second inner rod 36b via a second transmission rod 41b.

Process 1200 continues by installing the volume and/or pressure-controlled manual ventilator 10 within the storage case 20 in step 1206. The manual ventilator 10 including the compressible body, an output one-way valve 62 at an output end, and an input one-way valve 63 at an input end. In some embodiments, the manual ventilator 10 includes an output connector 65 communicatively coupled to the output one-way valve 62. In some embodiments, the output connector 65 is configured to be coupled to a patient interface 66. In some embodiments, the manual ventilator 10 includes a pressure-relief valve 64 proximal the output end.

Process 1200 continues by inputting automated ventilator settings into a logic circuit and/or microprocessor controlling the actuating mechanism, such that a tidal volume setting on the volume and/or pressure-controlled manual ventilator 10 governs throughout automated ventilation in step 1208. Process 1200 finishes by applying, by the logic circuit and/or microprocessor controlling the actuating mechanism, pressure to the compressible body of the manual ventilator 10 such that the volume specified by the tidal volume setting on the volume and/or pressure-controlled manual ventilator 10 is delivered by compression of the compressible body as it is deflated in step 1210. For example, in some embodiments, the actuating mechanism is configured to convert a rotating motion of the power unit 30 into an axial movement of the linear rod mechanism. In some embodiments, the actuating mechanism applies pressure to the compressible body of the manual ventilator via the one or more applicator pads 42 such that a volume of the compressible body of the manual ventilator 10 is deflated.

One skilled in the art will realize the invention can be embodied in other specific forms without departing from the spirit or essential characteristics thereof. The foregoing embodiments are therefore to be considered in all respects illustrative rather than limiting of the invention described herein. It will be appreciated that the illustrated embodiments and those otherwise discussed herein are merely examples of the invention and that other embodiments, incorporating changes thereto, including combinations of the illustrated embodiments, fall within the scope of the invention.

What is claimed:

1. A system for actuating a volume and/or pressure-controlled manual ventilator, the system comprising:
   a manual ventilator comprising a compressible body, an output one-way valve at an output end, and an input one-way valve at an input end;
   a storage case comprising an inner housing surface and an outer housing surface, the inner housing surface configured to accommodate the manual ventilator; and
   an actuating mechanism comprising:
      a power unit mechanically coupled to a linear actuation means, wherein the power unit is fitted with a dual-channel pulley configured to transmit rotational force to the linear actuation means via one or more belt or chains;
      the linear actuation means configured to convert a rotating motion of the power unit into an axial movement of the linear actuation means; and
      one or more applicator pads mechanically coupled to the linear actuation means and proximal to the compressible body of the manual ventilator;
   wherein the actuating mechanism is configured to apply pressure to the compressible body of the manual ventilator via the one or more applicator pads such that a volume of the compressible body is deflated.

2. The system of claim 1, wherein the manual ventilator comprises an output connector communicatively coupled to the output one-way valve, the output connector configured to be coupled to a patient interface.

3. The system of claim 1, wherein the manual ventilator comprises a pressure-relief valve proximal the output end.

4. The system of claim 1, wherein the inner housing surface of the storage case comprises one or more anchoring points for the actuating mechanism.

5. The system of claim 1, wherein the power unit comprises an electrical servo-type motor.

6. The system of claim 1, wherein the linear actuation means is mechanically coupled to the one or more belt or chains via one or more receiving pulleys.

7. The system of claim 1, wherein the linear actuation means comprises a first outer housing mechanically coupled to a first inner rod and a second outer housing mechanically coupled to a second inner rod.

8. The system of claim 7, wherein a first of the one or more applicator pads is mechanically coupled to the first inner rod and a second of the one or more applicator pads is mechanically coupled to the second inner rod.

9. The system of claim 8, wherein the first of the one or more applicator pads is mechanically coupled to the first inner rod via a first transmission rod and the second of the one or more applicator pads is mechanically coupled to the second inner rod via a second transmission rod.

10. A method for actuating a volume and/or pressure-controlled manual ventilator, the method comprising:
   providing a storage case comprising an inner housing surface and an outer housing surface, the inner housing surface configured to accommodate a manual ventilator;
   providing an actuating mechanism comprising a power unit mechanically coupled to a linear actuation means, and one or more applicator pads mechanically coupled to the linear actuation means and proximal to a compressible body of the manual ventilator, wherein the power unit is fitted with a dual-channel pulley configured to transmit rotational force to the linear actuation means via one or more belt or chains;
   installing the manual ventilator within the storage case, the manual ventilator comprising the compressible body, an output one-way valve at an output end, and an input one-way valve at an input end;
   inputting automated ventilator settings, wherein a tidal volume setting on the manual ventilator governs throughout automated ventilation;
   converting, by the linear actuation means, a rotating motion of the power unit into an axial movement of the linear actuation means; and applying, by the actuating mechanism, pressure to the compressible body of the manual ventilator via the one or more applicator pads such that a volume of the compressible body is deflated.

11. The method of claim 10, wherein the manual ventilator comprises an output connector communicatively coupled to the output one-way valve, the output connector configured to be coupled to a patient interface.

12. The method of claim 10, wherein the manual ventilator comprises a pressure-relief valve proximal the output end.

13. The method of claim 10, wherein the inner housing surface of the storage case comprises one or more anchoring points for the actuating mechanism.

14. The method of claim 10, wherein the power unit comprises an electrical servo-type motor.

15. The method of claim 10, wherein the linear actuation means is mechanically coupled to the one or more belt or chains via one or more receiving pulleys.

16. The method of claim 10, wherein the linear actuation means comprises a first outer housing mechanically coupled to a first inner rod and a second outer housing mechanically coupled to a second inner rod.

17. The method of claim 16, wherein a first of the one or more applicator pads is mechanically coupled to the first inner rod and a second of the one or more applicator pads is mechanically coupled to the second inner rod.

18. The method of claim 17, wherein the first of the one or more applicator pads is mechanically coupled to the first inner rod via a first transmission rod and the second of the one or more applicator pads is mechanically coupled to the second inner rod via a second transmission rod.

19. A method for mechanically actuating a volume and/or pressure controlled manual ventilator, the method comprising:

providing a storage case comprising an inner housing surface and an outer housing surface, the inner housing surface configured to accommodate a volume and/or pressure-controlled manual ventilator;

providing an actuating mechanism comprising an electrical or pneumatic power unit mechanically coupled to linear actuation means capable of compressing a compressible body of the volume and/or pressure-controlled manual ventilator, wherein the power unit is fitted with a dual-channel pulley configured to transmit rotational force to the linear actuation means via one or more belt or chains, the linear actuation means configured to convert a rotating motion of the power unit into an axial movement of the linear actuation means;

installing the volume and/or pressure-controlled manual ventilator within the storage case, the manual ventilator comprising the compressible body, an output one-way valve at an output end, and an input one-way valve at an input end;

inputting automated ventilator settings into a logic circuit and/or microprocessor controlling the actuating mechanism, wherein a tidal volume setting on the volume and/or pressure-controlled manual ventilator governs throughout automated ventilation; and applying, by the logic circuit and/or microprocessor controlling the actuating mechanism, pressure to the compressible body of the manual ventilator, wherein the volume specified by the tidal volume setting on the volume and/or pressure controlled manual ventilator is delivered by compression of the compressible body during deflation.

* * * * *